United States Patent [19]
Brown

[11] Patent Number: 5,439,929
[45] Date of Patent: Aug. 8, 1995

[54] BICYCLIC CARBAMATES, PHARMACEUTICAL COMPOSITIONS AND USE

[75] Inventor: Matthew F. Brown, Pawcatuck, Conn.

[73] Assignee: Pfizer Inc., New York, N.Y.

[21] Appl. No.: 204,037

[22] Filed: Mar. 1, 1994

[51] Int. Cl.$^6$ .................. A61K 31/40; A61K 31/415; C07D 209/08; C07D 231/56

[52] U.S. Cl. .................. 514/403; 514/415; 548/361.1; 548/469; 548/490

[58] Field of Search .................. 548/361.1, 469, 490; 514/403, 413

[56] References Cited

U.S. PATENT DOCUMENTS 5,280,039  1/1994  Eggler .

FOREIGN PATENT DOCUMENTS 0179619   3/1986  European Pat. Off. .
0199543  10/1986  European Pat. Off. .
0227241   7/1987  European Pat. Off. .
0455596  11/1991  European Pat. Off. .
0539329   3/1993  European Pat. Off. .

*Primary Examiner*—Robert W. Ramsuer
*Attorney, Agent, or Firm*—Peter C. Richardson; Gezina Holtrust; B. Timothy Creagan

[57] ABSTRACT

The present invention relates to bicyclic carbamate compounds and, specifically, to compounds of the formula

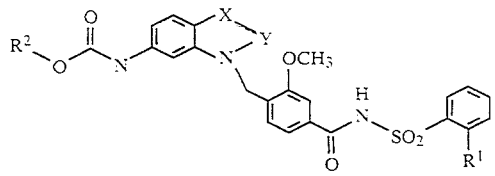

wherein X, Y, $R^1$ and $R^2$ are as defined in the specification. The compounds of this invention are useful in the treatment of asthma, rheumatoid arthritis, osteoarthritis, bronchitis, chronic obstructive airways disease, psoriasis, allergic rhinitis, atopic dermatitis, shock, other inflammatory diseases, and other conditions where the treatment is effected or facilitated by blocking the leukotriene D4 receptor.

13 Claims, No Drawings

BICYCLIC CARBAMATES, PHARMACEUTICAL COMPOSITIONS AND USE

BACKGROUND OF THE INVENTION

The present invention relates to bicyclic carbamates and related compounds, pharmaceutical compositions comprising such compounds, and the use of such compounds as antagonists of leukotriene D4. The compounds of this invention are useful in the treatment of asthma, rheumatoid arthritis, osteoarthritis, bronchitis, chronic obstructive airways disease, psoriasis, allergic rhinitis, atopic dermatitis, shock, and other inflammatory diseases. This invention also relates to pharmaceutical compositions containing these compounds and to methods of blocking the leukotriene D4 receptor.

It is known that arachidonic acid (AA) is metabolized in mammals by two distinct pathways. The metabolism of arachidonic acid by cyclooxygenase enzymes results in the production of prostaglandins and thromboxanes. The other pathway of AA metabolism involves lipoxygenase enzymes and results in the production of a number of oxidative products called leukotrienes. The latter are designated by the LT nomenclature system, and one of the most significant products of the lipoxygenase metabolic pathway is the leukotriene D4. Leukotrienes participate in inflammatory reactions, exhibit chemotactic activities, stimulate lysosomal enzyme release and act as important factors in the immediate hypersensitivity reaction. For example, LTD4 is a potent bronchoconstrictor of the human bronchi.

The biological activity of the leukotrienes indicates that a rational approach to drug therapy to prevent, remove or ameliorate the symptoms of asthma, rheumatoid arthritis, osteoarthritis, bronchitis, chronic obstructive airways disease, psoriasis, allergic rhinitis, atopic dermatitis, shock and other inflammatory diseases must focus on either blocking the release of mediators of these conditions or antagonizing their effects. Thus, compounds which inhibit the biological effects of the leukotrienes are considered to be of value in treating such conditions defined above.

SUMMARY OF THE INVENTION

The present invention relates to a compound of the formula

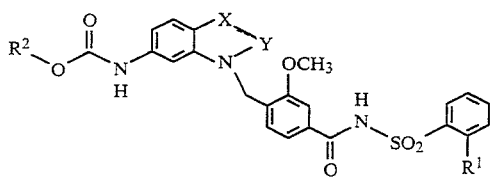

I and the pharmaceutically acceptable salts thereof, wherein the broken line represents an optional double bond; X is CH or $CH_2$ and Y is N, CH or $CH_2$, with the proviso that when X and Y are both CH or when X is CH and Y is N, the broken line represents a double bond; and with the proviso that when X is CH, than Y is CH and when X is $CH_2$, then Y is N or $CH_2$. $R^1$ is $(C_1-C_6)$alkyl, $(C_2-C_6)$alkenyl, $(C_2-C_6)$alkynyl, $(C_1-C_6)$alkoxy or $(C_2-C_6)$alkenyloxy and $R^2$ is a group of the formula

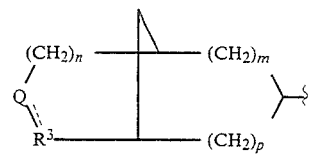

wherein the broken line represents an optional double bond; n is 0 or 1; m is 0, 1 or 2; p is 0, 1 or 2; Q is CH or $CH_2$ and $R^3$ is CH or $CH_2$, wherein $R^2$ is in an exo or endo configuration or a mixture thereof, with the proviso that when Q and $R^3$ are both CH, the broken line represents a double bond.

The term "alkyl", as used herein, unless otherwise indicated, includes saturated monovalent hydrocarbon radicals having straight, branched or cyclic moieties or combinations thereof. The term "alkenyl", as used herein, unless otherwise indicated, includes unsaturated hydrocarbon radicals having 1 to 3 double bonds, conjugated or nonconjugated in a cis or trans configuration, wherein said hydrocarbon radicals are straight, branched or cyclic moieties or combinations thereof.

The term "alkynyl", as used herein, unless otherwise indicated, includes unsaturated hydrocarbon radicals having 1 to 3 triple bonds, wherein said hydrocarbon radicals are straight or branched moieties or combinations thereof.

The term "alkoxy", as used herein, includes O-alkyl groups wherein "alkyl" is defined above.

The term "alkenyloxy", as used herein, includes O-alkenyl groups wherein "alkenyl" is defined above.

The compounds of formula I have chiral centers and therefore exist in different enantiomeric forms. This invention relates to all optical isomers and stereoisomers of the compounds of formula I and mixtures thereof.

Preferred compounds of formula 1 include those wherein n is 0, m is 1 and p is 0.

Other preferred compounds of formula I are those wherein X is CH, Y is N and $R^1$ is methyl.

Other preferred compounds of formula I are those wherein X and Y are both $CH_2$ and $R^1$ is methyl.

Other preferred compounds of formula I are those wherein X and Y are both CH and $R^1$ is methyl.

Other preferred compounds of formula I are those wherein $R^2$ is in an exo or endo configuration.

More preferred compounds of formula I are those wherein n is 0, m is 1, p is 0, X is CH, Y is N and $R^1$ is methyl.

More preferred compounds of formula I are those wherein n is 0, m is 1, p is 0, X is CH, Y is CH and $R^1$ is methyl.

More preferred compounds of formula 1 are those wherein n is 0, m is 1, p is 0, X is $CH_2$, Y is $CH_2$ and $R^1$ is methyl.

Specific preferred compounds of formula 1 include the following:

4-[[(6-exo-bicyclo[2.2.1]heptane-2-oxycarbonyl)amino]-indazol-1-yl]-methyl]-3-methoxy-N-o-tolylsulfonylbenzamide;

4-[[(6-endo-bicyclo[2.2.1]heptane-2-oxycarbonyl)amino]-indazol-1-yl]-methyl]-3-methoxy-N-o-tolylsulfonylbenzamide;

4-[[(6-exo-bicyclo[2.2.1]heptane-2-oxycarbonyl)amino]-indol-1-yl]-methyl]-3-methoxy-N-o-tolylsulfonylbenzamide;

4-[[(6-endo-bicyclo[2.2.1]heptane-2-oxycarbonyl-
)amino]-indol-1-yl]-methyl]-3-methoxy-N-o-tolylsul-
fonylbenzamide;

4-[[(6-exo-bicyclo[2.2.1]heptane-2-oxycarbonyl)amino]-
indolin-1-yl]-methyl]-3-methoxy-N-o-tolylsulfonyl-
benzamide;

4-[[(6-endo-bicyclo[2.2.1]heptane-2-oxycarbonyl-
)amino]-indolin-1-yl]-methyl]-3-methoxy-N-o-tolyl-
sulfonylbenzamide;

4-[[(6-exo-bicyclo[2.2.1]hept-5-en-2-oxycarbonyl-
)amino]-indazol-1-yl]-methyl]-3-methoxy-N-o-tolyl-
sulfonylbenzamide;

4-[[(6-endo-bicyclo[2.2.1]hept-5-en-2-oxycarbonyl-
)amino]-indazol-1-yl]-methyl]-3-methoxy-N-o-tolyl-
sulfonylbenzamide;

4-[[(6-exo-bicyclo[2.2.1]hept-5-en-2-oxycarbonyl-
)amino]-indol-1-yl]-methyl]-3-methoxy-N-o-tolylsul-
fonylbenzamide;

4-[[(6-endo-bicyclo[2.2.1]hept-5-en-2-oxycarbonyl-
)amino]-indol-1-yl]-methyl]-3-methoxy-N-o-tolylsul-
fonylbenzamide;

4-[[(6-exo-bicyclo[2.2.1]hept-5-en-2-oxycarbonyl-
)amino]-indolin-1-yl]-methyl]-3-methoxy-N-o-tolyl-
sulfonylbenzamide;

4-[[(6-endo-bicyclo[2.2.1]hept-5-en-2-oxycarbonyl-
)amino]-indolin-1-yl]-methyl]-3-methoxy-N-o-tolyl-
sulfonylbenzamide;

4-[[(6-exo-bicyclo[2.2.1]heptane-2-oxycarbonyl)amino]-
indol-1-yl]-methyl]-3-methoxy-N-o-ethenyloxy-
phenylsulfonylbenzamide;

4-[[(6-endo-bicyclo[2.2.1]heptane-2-oxycarbonyl-
)amino]-indol-1-yl]-methyl]-3-methoxy-N-o-
ethenyloxyphenylsulfonylbenzamide;

4-[[(6-exo-bicyclo[2.2.1]heptane-2-oxycarbonyl)amino]-
indazol-1-yl]-methyl]-3-methoxy-N-o-ethenyloxy-
phenylsulfonylbenzami;

4-[[(6-endo-bicyclo[2.2.1]heptane-2-oxycarbonyl-
)amino]-indazol-1-yl]-methyl]-3-methoxy-N-o-
ethenyloxyphenylsulfonylbenzamide;

4-[[(6-exo-bicyclo[2.2.1]heptane-2-oxycarbonyl)amino]-
indol-1-yl]-methyl]-3-methoxy-N-o-ethynylphenyl-
sulfonylbenzamide;

4-[[(6-endo-bicyclo[2.2.1]heptane-2-oxycarbonyl-
)amino]-indol-1-yl]-methyl]-3-methoxy-N-o-ethynyl-
phenylsulfonylbenzamide.

The present invention also relates to a pharmaceutical composition for treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising an amount of a compound of formula I effective in treating such a condition, and a pharmaceutically acceptable carrier.

The present invention also relates to a method of treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising administering to said mammal an amount of a compound of formula I effective in treating such a condition.

The present invention also relates to a pharmaceutical composition for blocking the leukotriene D4 receptor in a mammal, including a human, comprising a leukotriene D4 receptor blocking amount of a compound of formula I and a pharmaceutically acceptable carrier.

The present invention also relates to a method of blocking the leukotriene D4 receptor in a mammal, including a human, comprising administering to said mammal a leukotriene D4 receptor blocking amount of a compound of formula I.

The present invention also relates to a pharmaceutical composition for treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising an amount of a compound of formula I effective in blocking the leukotriene D4 receptor, and a pharmaceutically acceptable carrier.

The present invention also relates to a method of treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases in a mammal, including a human, comprising administering to said mammal an amount of a compound of formula I effective in blocking the leukotriene D4 receptor.

The present invention also relates to a pharmaceutical composition for treating a disorder in a mammal, including a human, the treatment of which is effected or facilitated by blocking the leukotriene D4 receptor, comprising an amount of a compound of formula I effective in treating such disorder, and a pharmaceutically acceptable carrier.

The present invention also relates to a method of treating a disorder in a mammal, including a human, the treatment of which is effected or facilitated by blocking the leukotriene D4 receptor, comprising administering to said mammal an amount of a compound of formula I effective in treating such a disorder.

DETAILED DESCRIPTION OF THE INVENTION

The following reaction scheme illustrates the preparation of the compounds of the present invention. Unless otherwise indicated X, Y, $R^1$ and $R^2$ in the reaction schemes and discussion that follow are defined as above.

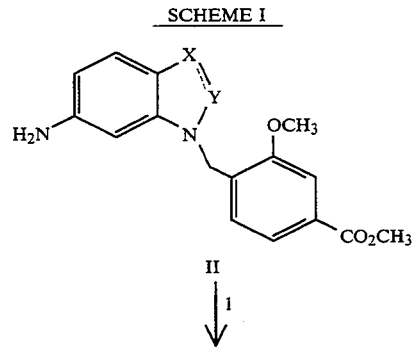

-continued
SCHEME I

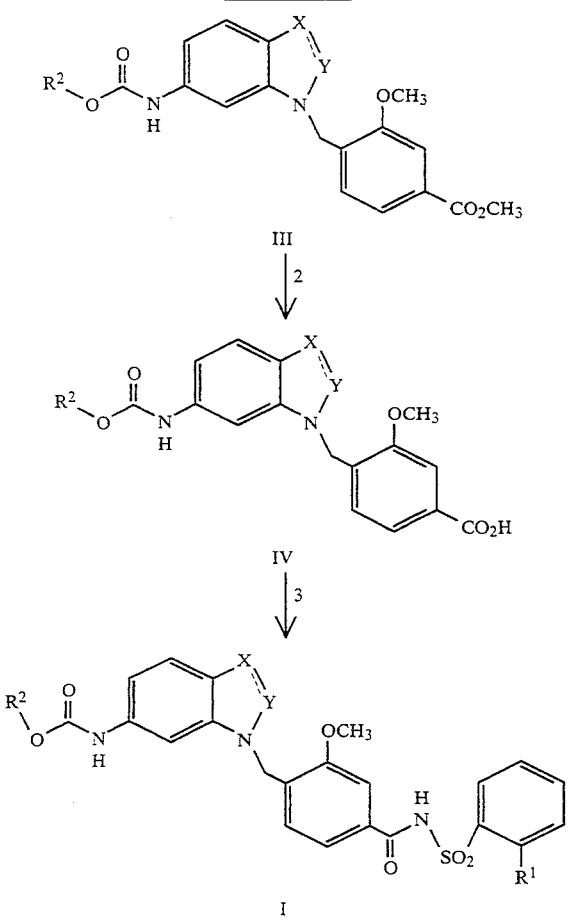

The compounds of formula II, the starting material used in Scheme 1, may be prepared as described in Matassa, V. G., et al., *J. Med. Chem.*, 33, 2621 (1990) and Brown, F. J., et al., *J. Med. Chem.*, 33, 1771 (1990).

In reaction 1 of Scheme I, the compound of formula II is converted to the corresponding bicyclic(oxycarbonyl)amino compound of formula III by reacting II with an exo or endo bicyclic chloroformate of the formula

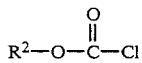

wherein $R^2$ is defined with reference to formula I, and N-methylmorpholine in a polar aprotic solvent such as dichloromethane. The reaction is stirred, at room temperature, for a time period between about 15 minutes to about 6 hours, preferably about 30 minutes.

In reaction 2 of Scheme 1, the compound of formula III is converted to the corresponding 3-methoxybenzoic acid compound of formula IV by reacting III with aqueous lithium hydroxide in a methanol/water/tetrahydrofuran solution. The reaction mixture is stirred at room temperature for a time period between about 15 hours to about 30 hours, preferably about 24 hours.

In reaction 3 of Scheme 1, the compound of formula IV is converted to the 3-methoxy-N-o-tolylsulfonylbenzamide compound of formula I by reacting IV with a sulfonamide, preferably o-tolylsulfonamide, a carbodiimide such as dicyclohexylcarbodiimide or 1-(3-dimethylaminopropyl)-3-ethylcarbodiimide, preferably 1-(3-dimethylaminopropyl)-3-ethylcarbodiimide, and 4-dimethylaminopyridine, in a polar aprotic solvent, preferably dichloromethane. The resulting reaction mixture is stirred for a time period between about 15 hours to about 30 hours, preferably about 24 hours, at a temperature between about 0° C. to about room temperature, preferably room temperature.

The compounds of the formula I and their pharmaceutically acceptable salts (hereinafter also referred to as the compounds of the present invention) are useful as selective antagonists of leukotriene D4, i.e., they possess the ability to block the leukotriene D4 receptor in mammals, and therefore they are able to function as therapeutic agents in the treatment of the aforementioned disorders and diseases in an afflicted mammal.

The compounds of the present invention are believed to be antagonists of leukotriene D4 and therefore are of value in the treatment of a wide variety of clinical conditions the treatment of which are effected or facilitated by blocking the leukotriene D4 receptor. Such conditions include asthma, rheumatoid arthritis, osteoarthritis, bronchitis, chronic obstructive airways disease, psoriasis, allergic rhinitis, atopic dermatitis, shock, and other inflammatory diseases. Hence, these compounds are readily adapted to therapeutic use as selective antagonists of leukotriene D4 for the control and/or treatment of any of the aforesaid clinical conditions in mammals, including humans.

The compounds of the present invention are readily adapted to clinical use as selective antagonists of leukotriene D4. The ability of the compounds or the pharmaceutically acceptable salts thereof to block the leukotriene D4 receptor may be shown by the following in vitro calcium mobilization assay. U-937 cells are grown in 50% RPMI 1640, 50% ethylene glycol dimethyl ether plus 5% heat inactivated FBS, 2 mM 1-glutamine, 100 units/100 μg Pen/Strop and 20 mM 4-(2-hydroxyethyl)-1-piperazine-ethanesulfonic acid (pH=7.4). Two to four days prior to the experiment, U-937 cells are incubated with 1.3% methyl sulfoxide, a treatment which is reported to cause chemotaxis and lysosomal enzyme release in response to chemical mediators (see: Kay et al., *Infect. Immun.*, 41, 1166, (1983)). It appears that U-937 cells are induced to differentiate functionally to a human monocyte-like cell line by the methyl sulfoxide treatment. The cells are seeded at densities of $3-8 \times 10^5$ cells/ml in 50% RPMI 1640, 50% ethylene glycol dimethyl ether plus 10% heat inactivated FBS, 2 ml glutamine, 100 units/100 μg Pen/Strep, 20 mM 4-(2-hydroxyethyl)-1-piperazine-ethanesulfonic acid (pH=7.4) and 1.3% methyl sulfoxide in spinner culture at 37° C. and grown in a closed system.

Differentiated U-937 cells are harvested on days 2, 3 or 4 by centrifugation at 1000 rpm for 5 minutes. After washing 3 times with a Krebs-Ringer-Hensleit buffer solution, cells ($6-12 \times 10^7$) are resuspended in 15 ml of the buffer (118 mM sodium chloride, 4.6 mM potassium chloride, 1.1 mM magnesium chloride, 1 mM calcium chloride, 5 mM 4-(2-hydroxyethyl)-1-piperazine-ethanesulfonic acid, 24.9 mM sodium hydrogen carbonate, 1 mM potassium hydrogen phosphate, 11.1 mM D-glucose and 0.1% bis(trimethylsilyl)acetamide, pH=7.4). To this cell suspension is added 10 ml of Krebs-Ringer-Hensleit buffer containing 50 μl of fura-2/AM [Molecular Probes Catalog #F-1221, 50 μg/vial, dissolved in 50 μl of silylation grade methyl sulfoxide (Pierce)] prior to an addition to the buffer. The cell mixture is then incubated at 37° C. for 30 minutes. At the end of incubation, 25 ml of warmed Krebs-Ringer-Hensleit buffer (37° C.) is added and the cell suspension is centrifuged at 1000 rpm for 5 minutes. The supernatant is discarded and the cells are resuspended in fresh warm Krebs-Ringer-Hensleit buffer. The cell suspension is incubated for an additional 15 minutes at 37° C. to allow for complete hydrolysis of the intracellular fura-2 ester. Twenty-five mls of cold Krebs-Ringer-Hensleit buffer is then added for and the sample is centrifuged at 1000 rpm for 5 minutes. The cells are resuspended at a final concentration of $1 \times 10^7$ cells/ml in cold Krebs-Ringer-Hensleit buffer and kept at 4° C. until use for fluorescence determination.

The $[Ca^{2+}]i$ response is measured by an SLM DMX-100TM spectrofluorometer using an SLM-AMINCO Ion Quantitation Software (Version 3.5). To set up the instrument, 1.8 ml of warmed Krebs-Ringer-Hensleit buffer plus 0.1 ml of fura-2 loaded U-937 cell suspension is placed in a curvette chamber containing a magnetic stir bar. Within the calcium software, the integration is set at 0.9 seconds and the gain on Channel A equal to 100, and adjusted the frequency such that Channel A read approximately $4.5-5.0 \times 10^4$ (Channel B automatically changes itself). At the beginning of each experiment, an $R_{max}$ is determined (by addition of 10 μl of 10% Triton X-100 to the curvette which contained 1.8 ml warm Krebs-Ringer-Hensleit buffer plus 0.1 ml fura-2 loaded cells) followed by $R_{min}$ (by addition of 100 mM of ethylenebis(oxyethylenenitrilo)tetraacetic acid to the $R_{max}$ curvette). These values are used by the software to determine $[Ca^{2+}]i$ concentration from the ratio of fura-2 emission intensities at two excitation wavelengths (a ratio of 340 nm to 380 nm). After setting the frequency for channel A and then determining $R_{max}$ and $R_{min}$, the machine is ready for acquiring $[Ca^{2+}]i$ values. A curvette containing 1.8 ml of warmed Krebs-Ringer-Hensleit buffer and 0.1 ml of cell suspension ($2 \times 10^6$ cells) is placed in the warmed curvette holder. The chamber is then closed and the shutters opened. The software began to acquire a $[Ca^{2+}]i$ signal from 0 to 20 seconds. After injection of either drug or methyl sulfoxide vehicle (2 μl) via a special port, the incubation is continued for 180 seconds as the signal is still being recorded. At exact 200 seconds an agonist (dissolved in methyl sulfoxide, 2-6 μl) is injected into the curvette through the same port and the signal is recorded for an additional 100 seconds (Total run time=5 minutes). $[Ca^{2+}]i$ values are determined by the software (3.5 version).

The ability of the compounds of formula I to compete with radiolabelled LTD4 for specific receptor cites on guinea pig lung membranes may be tested as described by Cheng et al, Biochemical and Biophysical Research Communication, 118, 1, 20-26 (1984).

To evaluate the compounds of the formula I in vivo, they are tested by the aerosolized antigen induced airway obstruction assay procedure.

Male Hartley guinea pigs (300-250 grams) are passively immunized by subcutaneous injection of 0.375 mg/kg of purified guinea pig anti-ovalbumin IgG1, 48-72 hours prior to antigen challenge. Pyrilamino (5 mg/kg) and propranolol (2 mg/kg) are administered subcutaneously 30 minutes prior to challenge. Test compounds are administered into the stomach, either one or two hours prior to challenge, as a suspension in water and 2% Tween-80 using an Argyle feeding tube.

Guinea pigs (5/test dose+5 controls) are then placed in a Tri-R Airborne infection apparatus (model A42). Ovalbumin (OA, 0.01-0.03%)is dissolved in 0.9% saline, placed in the glass nobulizer-venturi unit and aerosol generated for 5 minutes (main air flowmeter set at 10). This is followed by a 8 minute cloud decay (vacuum flow set at 7.0).

After removal, animals are killed by injection of approximately 2 ml sodium pentobarbital. Animals die within 1 to 2 minutes of injection. As soon as they die, the animals' pleural spaces are opened by cutting into the xyphoid process allowing the lungs to collapse. Lungs are then removed, the heart cut away, and the trachea tied. The volume of air trapped air in the lungs is determined by measuring the upward force exerted on a 20 gram anchor, when the lungs and anchor are submerged in saline. The volume of trapped gas is normalised to the animals body weight and expressed as excised lung gas volume (ELGV)in ml/kg.

A test compound's performance is judged by its ability to reduce the drug treated group mean ELGV below that of the control group mean ELGV. A loglinear regression $$ELGV = slope \bullet log(dose) + intercept$$

is performed on the grouped mean data and an $ED_{50}$ is calculated as the dose necessary to produce a 50% reduction below the control group ELGV.
$ELGV 50\% = ((\text{control ELGV} - 2)/2) + 2)$ Data is reported either as the ED5o or as the % reduction in control ELGV $$\% \text{ reduction} = (\text{control ELGV} - \text{test drug ELGV})/(\text{control ELGV} - 2)$$

at a given test drug dose.

For treatment of the various conditions described above, the compounds of the present invention can be administered to the patient either alone or, preferably, in combination with pharmaceutically acceptable carriers or diluents in a pharmaceutical composition according to standard pharmaceutical practice. Such administration may be carried out in single or multiple doses. A compound can be administered via a variety of conventional routes of administration including orally, parenterally, by inhalation, and topically. When the compounds are administered orally, the dose range will generally be from about 0.5 to about 50 mg/kg/day for an average adult patient, preferably from about 2 to about 20 mg/kg/day in single or divided doses. If parenteral administration is desired, then an effective dose will generally be from about 0.5 to about 50 mg/kg/day. For intranasal or inhaler administration, the dosage will generally be formulated as a 0.1 to 1% (w/v) solution given in an amount of about 100 to about 1,000 μg/dose given 1 to 4 times daily. The compounds of formula I can also be administered topically in an ointment or cream in concentrations of about 0.5 to about 1%, generally applied 2 or 3 times per day to the affected area. In some instances it may be necessary to use dosages outside these limits, since the dosage will necessarily vary according to the species, age, weight, and response of the individual patient, severity of the patient's symptoms, potency of the particular compound being administered, type of pharmaceutical formulation chosen, and time period and interval at which administration is carried out.

The compounds of the present invention can be administered in a wide variety of different dosage forms, such as in the form of tablets, powders, lozenges, troches, hard candies, sprays, creams, salves, suppositories, jellies, gels, pastes, lotions, ointments, syrups or capsules, aqueous solutions or suspensions, injectable solutions, elixirs, and the like. Such carriers include solid diluents or fillers, sterile aqueous media and various non-toxic organic solvents, etc. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered (preferably pH greater than 8) if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically and this may preferably be done by way of creams, jellies, gels, pastes, ointments and the like, in accordance with standard pharmaceutical practice.

The present invention is illustrated by but is not limited to the specific details of the following Examples and Preparations. All melting points are uncorrected.

PREPARATIONS

The norbornylchloroformates were prepared by treating the corresponding norbornyl alcohols with phosgene in toluene. The enantiomerically pure chloroformates were prepared from enantiomerically pure norbornyl alcohols. The exo alcohols were prepared from the enantiomerically pure endo alcohols (the endo alcohols may be prepared as described in EP 428,302) by C-2 inversion via the Mitsunobu reaction.

PREPARATION A (+)-endo-bicyclo[2.2.1]heptan-2-ol

A solution containing (+)-endo-bicyclo[2.2.1]hept-5-en-2-ol (4.0 grams, 36.4 mmol) and 19% palladium on carbon (2 grams)in methanol (50 mL) was hydrogenated at 30 psi for 1 hour at ambient temperature. The resulting solution was filtered through celite and concentrated to give the titled compound (3.87 grams, 87%). $^1$H NMR (CDCl$_3$, 300 MHz)$\delta$4.25–4.15 (m, 1H), $\delta$2.2. (s, 2H), $\delta$2.18–2.10 (m, 1H), $\delta$2.00–1.78 (m, 2H), $\delta$1.60–1.45 (m, 1H), $\delta$1.40–1.20 (m, 4H), $\delta$0.87–0.76 (m, 1H).

PREPARATION B (+)-exo-bicyclo[2.2.1]heptan-2-ol

To a solution of (+)-endo-bicyclo[2.2.1]heptan-2-ol (2.0 grams, 17.8 mmol), triphenylphosphine (23.3 grams, 89.0 mmol) and p-nitrobenzoic acid (13.1 grams, 78.3 mmol) in benzene (75 mL) was added diethylazodicarboxylate (14.0 mL, 89.0 mmol). The reaction was stirred at room temperature for 48 hours, then concentrated. Chromatography on silica gel gave the p-nitrobenzoate ester (4.7 grams, 100%).

To a solution of the p-nitrobenzoate ester (4.5 grams, 17.2 mmol)in methanol (30 mL) was added 5 M sodium hydroxide (2 mL). The resulting solution was warmed to reflux for 10 minutes, then cooled. The solution was concentrated in vacuo and the crude taken up in ethyl acetate. The ethyl acetate solution was washed with water and saturated brine, then dried over magnesium sulfate. Concentration gave the titled compound (1.45 grams, 75%) as an off-white solid. $^1$H NMR (CDCl$_3$, 300 MHz) $\delta$3.74 (m, 1H), $\delta$2.26–2.21 (m, 1H)$\delta$2.13–2.12 (m, 1H), $\delta$1.68–1.20 (m, 6H), $\delta$1.13–1.08 (m, 1H), $\delta$1.04–0.96 (m, 2H); $^{13}$C NMR (CDCl$_3$, 75 MHz) $\delta$74.9, 44.3, 42.3, 35.4, 34.4, 28.1, 24.4.

PREPARATION C (+)-exo-bicyclo[2.2.1]heptan-2-oxycarbonyl chloride

To a solution of (+)-exo-bicyclo[2.2.1]heptan-2-ol (1.45 grams, 12.9 mmol)in toluene (10 mL) at 0° C. was added a solution of phosgene in toluene (7.4 mL, 14.2 mmol). The reaction was stirred 24 hours at ambient temperature. Concentration then gave the titled compound (1.63 grams, 74%). [α]$_D$=+7.2.

PREPARATIONS D–H

By the above described Preparations, the following compounds were prepared.

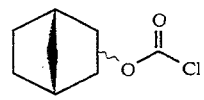

|  | CONFIGURATION OF NORBORNYL GROUP |
| --- | --- |
| Preparation D | (±)-exo |
| Preparation E | (±)-endo |
| Preparation F | (−)-exo |
| Preparation G | (+)-endo |
| Preparation H | (−)-endo |

PREPARATIONS I-L

By the above described Preparations, the following compounds were prepared.

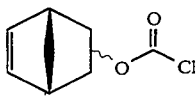

|  | CONFIGURATION OF NORBORNYL GROUP |
|---|---|
| Preparation I | (+)-exo |
| Preparation J | (−)-exo |
| Preparation K | (+)-endo |
| Preparation L | (−)-endo |

EXAMPLE 1

A. Methyl 3-methoxy4-[[(6-[bicyclo[2.2.1]heptan-2-oxycarbonyl)amino]-indazol-1-yl]-methyl]benzoate To a solution of 2-amino-indazol-1-yl-methylbenzoate (0.20 grams, 0.64 mmol) and N-methylmorpholine (0.07 mL, 0.64 mmol)in dichloromethane (5 mL) was added exo-bicyclo[2.2.1]heptan-2-oxycarbonyl chloride (0.71 grams, 0.64 mmol). The resulting solution was stirred at ambient temperature for 15 minutes. The reaction was quenched by addition of 1M hydrochloric acid and extracted with dichloromethane. The combined organics were dried over magnesium sulfate and concentrated. Chromatography on silica gel gave the titled compound (0.34 grams, 100%). $^1$H NMR (CDCl$_3$, 300 MHz) δ7.97 (s, 1H), δ7.89 (bs, 1H), δ7.60 (d, J=8.5 Hz, 1H), δ7.53 (d, J=1.4 Hz, 1H) δ7.47 (dd, J=7.8, 1.5 Hz, 1H), δ6.84–6.79 (m, 2H), δ6.73 (d, J=7.8 Hz, 1H), δ5.59 (s, 2H), δ4.63 (d, J=6.9 Hz, 1H) δ3.94 (s, 3H), δ3.87 (s, 3H), δ2.36 (d, J=4.5 Hz, 1H), δ2.30–2.25 (m, 1H), δ1.78–1.71 (m, 1H), δ1.59–1.35 (m, 4H), δ1.18–1.06 (m, 3H).

B. 4-[[(6-[bicyclo[2.2.1]heptan-2-oxycarbonyl)amino]-indazol-1-yl]-methyl]-3-methoxybenzoic acid To a solution of methyl 3-methoxy-4-[[(6-[bicyclo[2.2.1]heptan-2-oxycarbonyl)amino]-indazol-1-yl]-methyl]benzoate (0.28 grams, 0.62 mmol)in 12 mL of tetrahydrofuran/methanol/water (5:5:2) was added aqueous lithium hydroxide (0.13 grams, 3.1 mmol). The resulting solution was stirred 24 hours at ambient temperature, then concentrated in vacuo. The residue was treated with 1M hydrochloric acid, and the resulting white solid collected via filteration to give the titled compound (0.25 grams, 92%). Melting point 184°–188° C.; HRMS calculated for C$_{24}$H$_{25}$N$_3$O$_5$ 435.1794, found 435.1752.

C. 4-[[(6-[bicyclo[2.2.1]heptane-2-oxycarbonyl)amino]-indazol-1-yl]-methyl]-3-methoxy-N-o-tolylsulfonyl-benzamide A solution of 4-[[(6-[bicyclo[2.2.1]heptan-2-oxycarbonyl)amino]-indazol-1-yl]-methyl]-3-methoxybenzoic acid (0.20 grams, 0.46), o-tolylsulfonamide (0.079 grams, 0.46 mmol), 1-(3-dimethylaminopropyl)-3-ethylcarbodiimide (EDC)(0.13 grams, 0.69 mmol) and 4-dimethylaminopyridine (DMAP) (0.084 grams, 0.69 mmol) in dichloromethane (10 mL) was stirred 24 hours at ambient temperature. The reaction was quenched with 1M hydrochloric acid and extracted with dichloromethane. The combined organics were dried over magnesium sulfate, and concentrated. Chromatography on silica gel, followed by precipitating the product from a dichloromethane solution by rapid addition of pentane gave the title compound (0.23 grams, 87%). Melting point 224°–225° C. HRMS calculated for C$_{13}$H$_{32}$N$_4$O$_6$S 588.2043, found 588.1973.

EXAMPLES 2–13

By the method of Example 1, the following compounds were prepared.

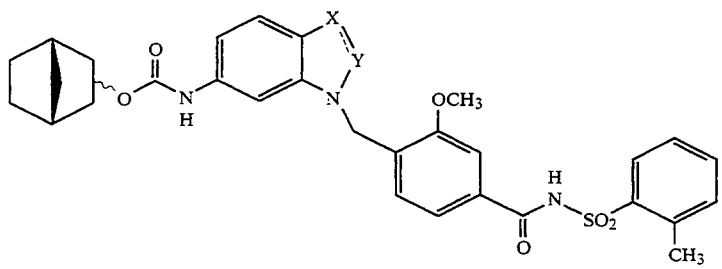

I

|  | CONFIGURATION OF NORBORNYL GROUP | X-Y |
|---|---|---|
| Example 2 | (±)-exo | —CH$_2$—CH$_2$— |
| Example 3 | (+)-exo | —CH$_2$—CH$_2$— |
| Example 4 | (±)-exo | —HC=CH— |
| Example 5 | (+)-exo | —HC=CH— |
| Example 6 | (−)-exo | —HC=CH— |
| Example 7 | (+)-endo | —HC=CH— |
| Example 8 | (−)-endo | —HC=CH— |
| Example 9 | (±)-endo | —HC=N— |
| Example 10 | (+)-exo | —HC=N— |
| Example 11 | (−)-exo | —HC=N— |
| Example 12 | (+)-endo | —HC=N— |
| Example 13 | (−)-endo | —HC=N— |

EXAMPLE 2

Analysis (%C,%H,%N): calculated: 63.24, 6.14, 6.91; found: 63.70, 6.19, 6.86. HRMS: calculated for C$_{32}$H$_{35}$N$_3$O$_6$S•H$_2$O 589.2247; found: 589.2216. Melting point (°C.): 125–135.

EXAMPLE 3

Analysis (%C,%H,%N): calculated: 65.20, 5.98, 7.13; found: 65.10, 6.51, 6.90. HRMS: calculated for C$_{32}$H$_{35}$N$_3$O$_6$S 589.2247; found: 589.2239. Melting point (°C.): 161–162.

EXAMPLE 4

Analysis (%C,%H,%N): calculated: 65.40, 5.66, 7.15; found: 64.84, 5.99, 6.87. HRMS: calculated for C$_{32}$H$_{33}$N$_3$O$_6$S 587.2090; found: 587.2101. Melting point (°C.): 137–143.

EXAMPLE 5

Analysis (%C,%H,%N): calculated: 65.40, 5.66, 7.15; found: 64.99, 6.21, 6.80. HRMS: calculated for C$_{32}$H$_{33}$N$_3$O$_6$S 587.2090; found: 587.2149. Melting point (°C.): 154–155.

EXAMPLE 6

HRMS: calculated for C$_{32}$H$_{33}$N$_3$O$_6$S 587.2090; found: 587.2063. Melting point (°C.): 162–163.

EXAMPLE 7

Analysis (%C,%H,%N): calculated: 65.40, 5.66, 7.15; found: 65.36, 6.06, 6.97. HRMS: calculated for C$_{32}$H$_{33}$N$_3$O$_6$S 587.2090; found: 587.2134. Melting point (°C.): 155–156.

EXAMPLE 8

Analysis (%C,%H,%N): calculated: 65.40, 5.66, 7.15; found: 65.00, 6.16, 6.72. HRMS: calculated for C$_{32}$H$_{33}$N$_3$O$_6$S 587.2090; found: 587.2040. Melting point (°C.): 160–161.

EXAMPLE 9

HRMS: calculated for C$_{31}$H$_{32}$N$_4$O$_6$S 588.2043; found: 588.2017. Melting point (°C.): 216–217.

EXAMPLE 10

Analysis (%C,%H,%N): calculated: 63.25, 5.48, 9.52; found: 63.04, 5.87, 9.47. HRMS: calculated for C$_{31}$H$_{32}$N$_4$O$_6$S 588.2043; found: 588.1963. Melting point (°C.): 183–184°.

EXAMPLE 11

Analysis (%C,%H,%N): calculated: 63.25, 5.48, 9.52; found: 63.22, 5.77, 9.47. HRMS: calculated for C$_{31}$H$_{32}$N$_4$O$_6$S 588.2043; found: 588.2042. Melting point (°C.): 177–178°.

EXAMPLE 12

HRMS: calculated for C$_{31}$H$_{32}$N$_4$O$_6$S 588.2043; found: 588.2001. Melting point (°C.): 174–175.

EXAMPLE 13

Analysis (%C,%H,%N): calculated: 61.37, 5.65, 9.23; found: 61.05, 5.88, 8.62. HRMS: calculated for C$_{31}$H$_{32}$N$_4$O$_6$S•H$_2$O 588.2043; found: 588.1963. Melting point (°C.): 164–165°.

EXAMPLES 14–20

By the method of Example 1, the following compounds were prepared.

| | CONFIGURATION OF NORBORNYL GROUP | X-Y |
|---|---|---|
| Example 14 | (+)-exo | —CH=CH— |
| Example 15 | (+)-endo | —CH=CH— |
| Example 16 | (−)-endo | —CH=CH— |
| Example 17 | (+)-exo | —CH=N— |
| Example 18 | (−)-exo | —CH=N— |
| Example 19 | (+)-endo | —CH=N— |
| Example 20 | (−)-endo | —CH=N— |

EXAMPLE 14

Analysis (%C,%H,%N): calculated: 65.62, 5.34, 7.17; found: 65.36, 6.04, 6.82. HRMS: calculated for C$_{32}$H$_{31}$N$_3$O$_6$S 585.1934; found: 585.1986. Melting point (°C.): 174 (compound foamed at this temperature).

EXAMPLE 15

HRMS: calculated for C$_{32}$H$_{31}$N$_3$O$_6$S 585.1934; found: 585.1951. Melting point (°C.): 184 (compound foamed at this temperature).

EXAMPLE 16

Analysis (%C,%H,%N): calculated: 63.67, 5.51, 6.97; found: 64.26, 5.62, 6.92. HRMS: calculated for C$_{32}$H$_{31}$N$_3$O$_6$S 585.1934; found: 585.1875. Melting point (°C.): 188 (compound foamed at this temperature).

EXAMPLE 17

HRMS: calculated for C$_{31}$H$_{30}$N$_4$O$_6$S 586.1886; found: 586.1910. Melting point (°C.): 186–187.

EXAMPLE 18

Analysis (%C,%H,%N): calculated: 63.47, 5.15, 9.55; found: 63.37, 5.43, 9.48. HRMS: calculated for C$_{31}$H$_{30}$N$_4$O$_6$S 586.1886; found: 586.1907. Melting point (°C.): 169–170.

EXAMPLE 19

HRMS: calculated for C$_{31}$H$_{30}$N$_4$O$_6$S 586.1886; found: 586.1953. Melting point (°C.): 163–164.

EXAMPLE 20

HRMS: calculated for C$_{31}$H$_{30}$N$_4$O$_6$S 586.1886; found: 586.1923. Melting point (°C.): 165–166.

I claim:
1. A compound of the formula

I

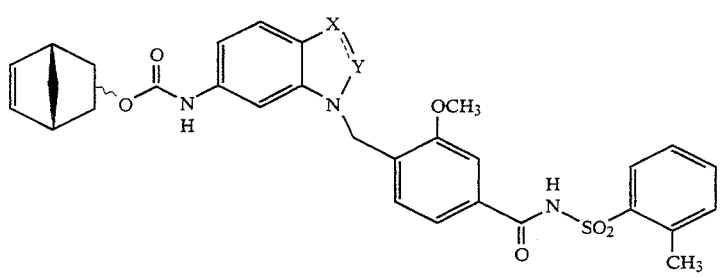

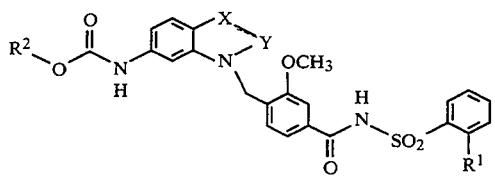

and the pharmaceutically acceptable salts thereof, wherein the broken line represents an optional double bond; X is CH or $CH_2$ and Y is N, CH or $CH_2$, with the proviso that when X and Y are both CH or when X is CH and Y is N, the broken line represents a double bond and with the proviso that when X is CH, then Y is CH and when X is $CH_2$, then Y is N or $CH_2$; $R^1$ is $(C_1-C_6)$alkyl, $(C_2-C_6)$alkenyl, $(C_2-C_6)$alkynyl, $(C_1-C_6)$alkoxy or $(C_2-C_6)$alkenyloxy and $R^2$ is a group of the formula

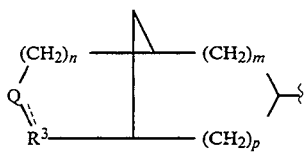

wherein the broken line represents an optional double bond; n is 0 or 1; m is 0, 1 or 2; p is 0, 1 or 2; Q is CH or $CH_2$ and $R^3$ is CH or $CH_2$, wherein $R^2$ is in an exo or endo configuration or m mixture thereof, with the proviso that when Q and $R^3$ are both CH, the broken line represents a double bond.

2. A compound according to claim 1, wherein n is 0, m is 1 and p is 0.

3. A compound according to claim 1, wherein X is CH, Y is N and $R^1$ is methyl.

4. A compound according to claim 1, wherein X and Y are both $CH_2$ and $R^1$ is methyl.

5. A compound according to claim 1, wherein X and Y are both CH and $R^1$ is methyl.

6. A compound according to claim 1, wherein $R^2$ is in an exo or endo configuration.

7. A compound according to claim 1, wherein n is 0, m is 1, p is 0, X is CH, Y is N and $R^1$ is methyl.

8. A compound according to claim 1, wherein n is 0, m is 1, p is 0, X is CH, Y is CH and $R^1$ is methyl.

9. A compound according to claim 1, wherein n is 0, m is 1, p is 0, X is $CH_2$, Y is $CH_2$ and $R^1$ is methyl.

10. A compound according to claim 1, said compound being selected from the group consisting of:

4-[[(6-exo-bicyclo[2.2.1]heptane-2-oxycarbonyl-)amino]-indazol-1-yl]-methyl]-3-methoxy-N-o-tolylsulfonylbenzamide;

4-[[(6-endo-bicyclo[2.2.1]heptane-2-oxycarbonyl-)amino]-indazol-1-yl]-methyl]-3-methoxy-N-o-tolylsulfonylbenzamide;

4-[[(6-exo-bicyclo[2.2.1]heptane-2-oxycarbonyl-)amino]-indol-1-yl]-methyl]-3-methoxy-N-o-tolylsulfonylbenzamide;

4-[[(6-endo-bicyclo[2.2.1]heptane-2-oxycarbonyl-)amino]-indol-1-yl]-methyl]-3-methoxy-N-o-tolylsulfonylbenzamide;

4-[[(6-exo-bicyclo[2.2.1]heptane-2-oxycarbonyl-)amino]-indolin-1-yl]-methyl]-3-methoxy-N-o-tolylsulfonylbenzamide;

4-[[(6-endo-bicyclo[2.2.1]heptane-2-oxycarbonyl-)amino]-indolin-1-yl]-methyl]-3-methoxy-N-o-tolylsulfonylbenzamide;

4-[[(6-exo-bicyclo[2.2.1]hept-5-en-2-oxycarbonyl-)amino]-indazol-1-yl]-methyl]-3-methoxy-N-o-tolylsulfonylbenzamide;

4-[[(6-endo-bicyclo[2.2.1]hept-5-en-2-oxycarbonyl-)amino]-indazol-1-yl]-methyl]-3-methoxy-N-o-tolylsulfonylbenzamide;

4-[[(6-exo-bicyclo[2.2.1]hept-5-en-2-oxycarbonyl-)amino]-indol-1-yl]-methyl]-3-methoxy-N-o-tolylsulfonylbenzamide;

4-[[(6-endo-bicyclo[2.2.1]hept-5-en-2-oxycarbonyl-)amino]-indol-1-yl]-methyl]-3-methoxy-N-o-tolylsulfonylbenzamide;

4-[[(6-exo-bicyclo[2.2.1]hept-5-en-2-oxycarbonyl-)amino]-indolin-1-yl]-methyl]-3-methoxy-N-o-tolylsulfonylbenzamide;

4-[[(6-endo-bicyclo[2.2.1]hept-5-en-2-oxycarbonyl-)amino]-indolin-1-yl]-methyl]-3-methoxy-N-o-tolylsulfonylbenzamide;

4-[[(6-exo-bicyclo[2.2.1]heptane-2-oxycarbonyl-)amino]-indol-1-yl]-methyl]-3-methoxy-N-o-ethenyloxyphenylsulfonylbenzamide;

4-[[(6-endo-bicyclo[2.2.1]heptane-2-oxycarbonyl-)amino]-indol-1-yl]-methyl]-3-methoxy-N-o-ethenyloxyphenylsulfonylbenzamide;

4-[[(6-exo-bicyclo[2.2.1]heptane-2-oxycarbonyl-)amino]-indazol-1-yl]-methyl]-3-methoxy-N-o-ethenyloxyphenylsulfonylbenzamide;

4-[[(6-endo-bicyclo[2.2.1]heptane-2-oxycarbonyl-)amino]-indazol-1-yl]-methyl]-3-methoxy-N-o-ethenyloxyphenylsulfonylbenzamide;

4-[[(6-exo-bicyclo[2.2.1]heptane-2-oxycarbonyl-)amino]-indol-1-yl]-methyl]-3-methoxy-N-o-ethynylphenylsulfonylbenzamide;

4-[[(6-endo-bicyclo[2.2.1]heptane-2-oxycarbonyl-)amino]-indol-1-yl]-methyl]-3-methoxy-N-o-ethynylphenylsulfonylbenzamide.

11. A pharmaceutical composition for blocking the leukotriene D4 receptor including a human i.e. a mammal comprising a leukotriene D4 receptor blocking amount of a compound of claim 1, and a pharmaceutically acceptable carrier.

12. A method of blocking the leukotriene D4 receptor in a mammal, including a human, comprising administering to said mammal a leukotriene D4 receptor blocking amount of a compound of claim 1.

13. A method according to claim 12 which comprises treating a condition selected from the group consisting of asthma, rheumatoid arthritis, osteoarthritis, bronchitis, chronic obstructive airways disease, psoriasis, allergic rhinitis, atopic dermatitis, shock, and other inflammatory diseases in a mammal.

* * * * *